United States Patent
Hoshino

(10) Patent No.: US 10,311,583 B2
(45) Date of Patent: Jun. 4, 2019

(54) EYE MOTION DETECTION METHOD, PROGRAM, PROGRAM STORAGE MEDIUM, AND EYE MOTION DETECTION DEVICE

(71) Applicant: Kiyoshi Hoshino, Tsukuba (JP)

(72) Inventor: Kiyoshi Hoshino, Tsukuba (JP)

(*) Notice: Subject to any disclaimer, the term of this patent is extended or adjusted under 35 U.S.C. 154(b) by 0 days.

(21) Appl. No.: 15/579,241

(22) PCT Filed: Jun. 3, 2016

(86) PCT No.: PCT/JP2016/066562
§ 371 (c)(1),
(2) Date: Dec. 4, 2017

(87) PCT Pub. No.: WO2016/195066
PCT Pub. Date: Dec. 8, 2016

(65) Prior Publication Data
US 2018/0174309 A1    Jun. 21, 2018

(30) Foreign Application Priority Data

Jun. 5, 2015  (JP) .................................. 2015-115287
Apr. 27, 2016  (JP) .................................. 2016-089759

(51) Int. Cl.
*G06T 7/246*  (2017.01)
*A61B 3/113*  (2006.01)
(Continued)

(52) U.S. Cl.
CPC .............. *G06T 7/248* (2017.01); *A61B 3/113* (2013.01); *G06T 7/11* (2017.01); *G06T 7/74* (2017.01); *G06T 2207/30041* (2013.01)

(58) Field of Classification Search
CPC ....... A61B 3/113; A61B 3/152; A61B 3/0025; A61B 3/14; G06T 7/11; G06T 7/248; G06T 7/74; G06T 2207/30041
(Continued)

(56) References Cited

U.S. PATENT DOCUMENTS 5,070,883 A * 12/1991 Kasahara ............... A61B 3/113
 351/209
9,433,345 B2    9/2016 Hoshino et al.
(Continued)

FOREIGN PATENT DOCUMENTS

JP      2164335 A     6/1990
JP      200899716 A   5/2008
WO      2013125704 A1 8/2013

OTHER PUBLICATIONS

Hashimoto et al.; "A Model of the Iris Pattern Stretches in Relation to Pupil Diameter and Its Application to Measurement of Roll Eye Movements"; Paper of the Institute of Electronics, Information and Communication Engineers; 2010; pp. 39-46; vol. J93-D:1.
(Continued)

*Primary Examiner* — Mekonen T Bekele
(74) *Attorney, Agent, or Firm* — The Webb Law Firm

(57) ABSTRACT

Provided is a method to easily detect eye motions in the eye moving direction, which has resistance to a fluctuation in background light and to a displacement of the position of a camera. The method includes the steps of: detecting a white area of the eye from the eye area; determining a blood vessel image to be used for a template blood vessel image in the white area of the eye; detecting a $n^{th}$ blood vessel image, which matches the template blood vessel image; calculating a $n^{th}$ moving amount of the eye based on a difference between the reference position and the detection position of the $n^{th}$ blood vessel image, which matches the template blood vessel image; and calculating a $n^{th}$ rotation angle of the eye to detect eye motions in the information processing apparatus.

20 Claims, 5 Drawing Sheets

(51) Int. Cl.
 *G06T 7/73* (2017.01)
 *G06T 7/11* (2017.01)
(58) Field of Classification Search
 USPC .......................................................... 382/107
 See application file for complete search history.

(56) References Cited

U.S. PATENT DOCUMENTS

| | | | |
|---|---|---|---|
| 2012/0050682 A1* | 3/2012 | Bonnin | A61B 3/113 351/210 |
| 2013/0162947 A1* | 6/2013 | Spasovski | A61B 3/0025 351/206 |
| 2014/0180162 A1* | 6/2014 | Schuhrke | A61B 3/0025 600/558 |
| 2018/0307277 A1* | 10/2018 | Yanagisawa | A61B 3/005 |

OTHER PUBLICATIONS

Nakagomi et al.; "Fast and Precise Measurement of Rotational Eye Movement by Detecting Conjunctiva Blood Vessel End"; The Transactions of the Institute of Electronics, Information and Communication Engineers D; 2013; pp. 876-884; vol. J96-D:4.

* cited by examiner

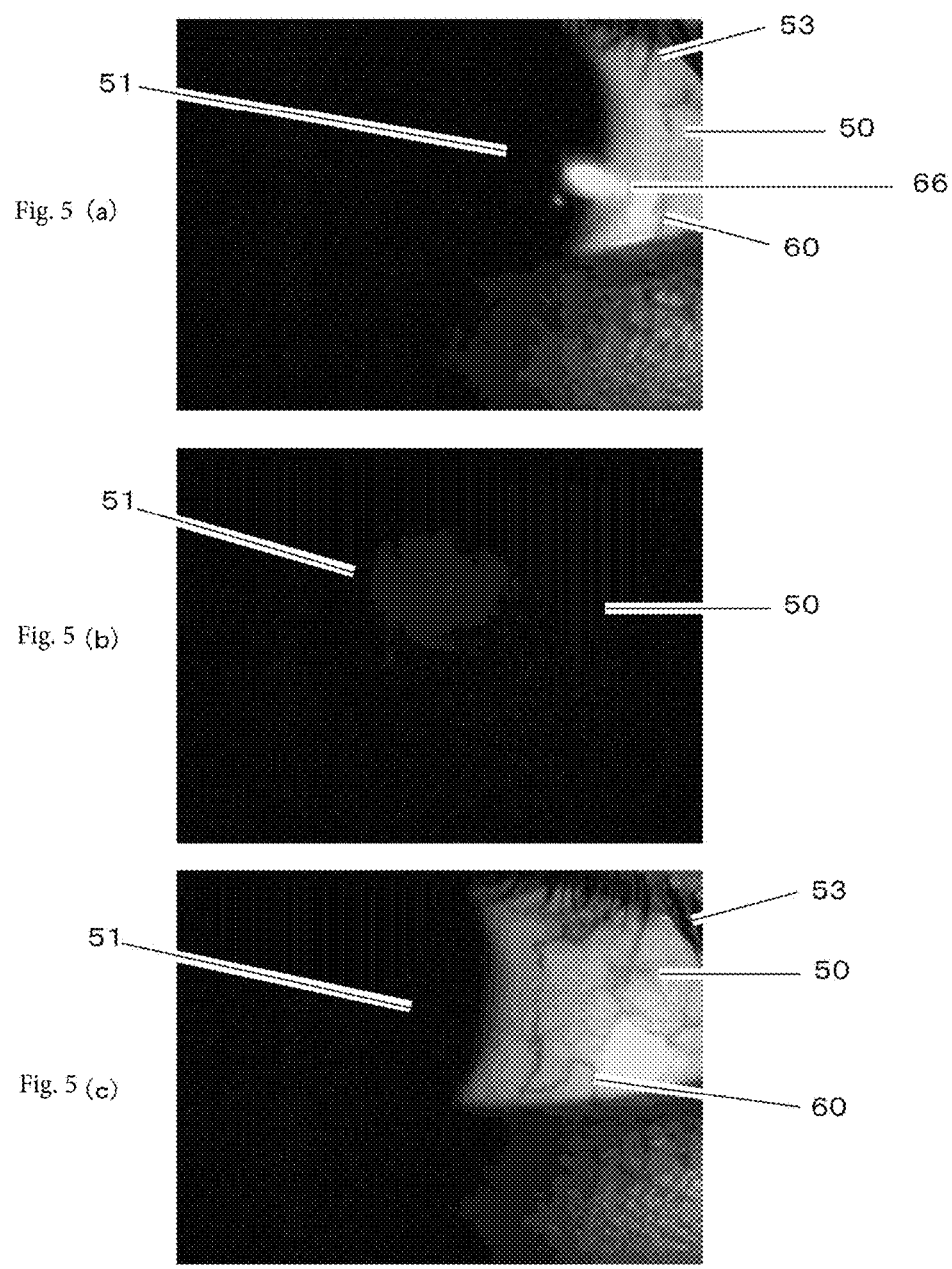

EYE MOTION DETECTION METHOD, PROGRAM, PROGRAM STORAGE MEDIUM, AND EYE MOTION DETECTION DEVICE

CROSS-REFERENCE TO RELATED APPLICATIONS

This application is the United States national phase of International Application No. PCT/JP2016/066562 filed Jun. 3, 2016, and claims priority to Japanese Patent Application Nos. 2015-115287 and 2016-089759, filed Jun. 5, 2015 and Apr. 27, 2016, respectively, the disclosures of which are hereby incorporated in their entirety by reference.

TECHNICAL FIELD

The present relates to an eye motion detection method for detecting eye motions on an image of a predetermined area around an eye captured by imaging device (camera) installed in the vicinity of the eye, and in particular, to a method for indirectly detecting the positions of the pupil of the eye or visual line directions and the like using feature points other than those of the iris and/or pupils of the eye on the eye image.

BACKGROUND ART

In recent years, a head-mounted display and a glass-type wearable device, both of which are equipped with a device for detecting eye motions, have been publicly known. Taking an instance of these devices, it is known that Google Glass (registered trademark), of which an infrared sensor is capable of detecting the upward motion and blink/wink of the eye, as well as attachment/detachment of a device, allows the user, depending on the settings, to take pictures or attach/detach a device by blinking and to switch a display on by moving the eyes upward In addition to devices for detecting eye motions such as blinking or winking to take an action, a method for detecting the position of the iris on the image of the area of the eye captured by a camera is known. Taking an instance, in order to detect the position of the iris of the eye, some devices use any of existing techniques such as template matching to match the iris on the eye image with the template image in terms of the iris pattern (grayscale pattern of the iris).

Moreover, the directions and speeds of eye motions may be detected by detecting the aforementioned position of the iris individually on the consecutive eye images and, for instance, projecting the individual positions in a 2-dimensional or 3-dimensional coordinate system to compare or find differences between consecutive coordinate values in the coordinate system. Furthermore, the aforementioned method, which allows the user to trace the direction of an eye motion or detects the patterns of the directions and speeds of eye motions and compares with known normal patterns to find a difference, if any, may have applications such as identification of any abnormality, bad condition or disease in the body. Taking an example, in normal cases, eye rotational motions (eye motions) occur along the visual line direction as a rotation axis when the tilted head returns to its original position. If the eye motions occur with the head not tilted, car sickness or motion sickness may be suspected (for instance, NPL 1).

Moreover, in some cases, when the image of an eye, of which surface is carved, is captured, the distance of a light path between the center of a target eye and a camera lens may vary, making it difficult to bring the camera into focus thereon and causing failure to focus when the eye moves. To solve this problem, one idea makes an attempt to use a camera with a large depth of focus in order to bring a whole area including the center of the eye and an area around the eye into focus. However, to this end, intense lighting is needed, which may affects the eyes. To address this problem, another idea has been designed so that the center of the pupil is detected and the focusing is controlled in connection with the center of the pupil to allow the focus to be correctly brought into the eye, even if it moves (for instance, PL 1).

Furthermore, one other method uses a cornea reflected image (Purkinjje's image), which take advantage of a difference in the center of rotation between the eye and cornea, to measure eye motions and the vertical and horizontal components of a visual line at a high accuracy.

In addition, the inventors of the present invention have proposed a method to measure eye rotations by identifying a blood vessel of a predetermined pattern in the vicinity of an iris in a white area (the portion, in which a sclerotic coat and a conjunctiva are exposed) of the eye in the reference state and detecting an outer peripheral edge of the iris based on the position of the end point of the identified blood vessel to solve the problem (described later) with aforementioned iris pattern detection (for instance, PL 2).

CITATION LIST

Non-Patent Literature

[NPL 1]
Tsutomu HASHIMOTO, Takao MAKI, Yusuke SAKASHITA, Junpei NISHIYAMA, Hironobu FUJIYOSHI, Yutaka HIRATA: "Modeling of Iris Pattern Erosion and Dilation based on Changes in Pupil Diameter and Application Thereof to Eye Motion Measurement", Paper of The Institute of Electronics, Information and Communication Engineers, pp. 39-46, No. 1, Vol. J93-D, 2010.

Patent Literature

[PL 1]
JP H02-164335 A
[PL 2]
International Patent (laid-open) No. WO2013/125707 pamphlet

SUMMARY OF INVENTION

Technical Problem

However, the iris pattern used in NPL 1 etc., has a disadvantage of its grayscale pattern being blur, and its shape, position and grayscale may vary with a change in pupil diameter in connection with the type of a target object to be watched and a change in light intensity of its periphery (background); thereby, it is required to stabilize the background light or block the background light by means of wearing a protective google to cover the area of the eye when the iris pattern is detected.

Moreover, PL 1 discloses one example of methods, which control focusing on an eye using the center of the pupil to bring the eye into focus even when the eye moves but information on the center of the pupil is used solely for focusing control. For this reason, PL 1 does not disclose the use of position information based on the center of the pupil in measuring the moving direction, moving amount, moving speed and like of the eye unlike the present invention.

Furthermore, a method using a corneal reflected image (Purkinjje's image) of the eye has a disadvantage of being affected easily by a moving amount between a head being measured and a camera, requiring firm fixation of the camera to the head with a belt and the like. In addition, this method using a corneal reflected image (Purkinjje's image) of the eye does not enable measurement of eye rotational motions.

Additionally, a method for measuring eye rotations disclosed in PL 2 may be able to solve the problem (difficult detection of a grayscale contrast pattern due to the background light, failure to measure a moving direction, etc. and difficult long-time firm fixation of a camera to the head) with the aforementioned methods disclosed in NPL 1 and PL 1 and using a corneal reflected image (Purkinjje's image) of the eye. However, since this method detects the outer peripheral end of the iris, the area, in which blood vessels to be used are contained, is limited to the vicinity of the iris. Moreover, the method has a restriction "at least part of the blood vessel has a point ending at the outer peripheral end of the iris". Furthermore, under such a restriction, it is required to identify a blood vessel of complicated shape (for instance, having a lot of kinks, branches and the like), which enables it to be discriminated from straight eyelashes projecting from a upper eye lid, and has a "thick size", which allows it to be detected as possible as easily, leading to high difficulty and long-time consumption in detecting blood vessels.

Additionally, taking an example, for a subject with a feature amount that the upper part of the iris is partially covered with the upper eye lid, as seen in a narrow distance between the upper and lower edges of the eye (subject with a slit eye), or a subject with a feature amount that the upper eyelashes are thick-colored, which may create a strong contrast, like black and long to the extent that they extend over the upper part of the iris or thick to the extent that they cover the upper part of the iris, favorable results of iris pattern detection may not be obtained in some cases. Generally, a great number of people (certain races of people) living in some areas in East Asia have often the aforementioned feature amounts and the subjects having such feature amounts are forced to intentionally open the eye widely or put up with blinking to measure the iris. Furthermore, the method disclosed in PL 2 has also failed to provide favorable results for people with the aforementioned feature amounts in some cases because the area, in which a blood vessel ending at an iris end, is narrow.

Accordingly, any conventional eye motion detection method has not satisfied all the requirements of: (1) capable of detecting a contrast grayscale pattern even when the background light fluctuated, (2) capable of long-time wearing with no need for firmly fixing a camera to the head, (3) easily detecting eye motions in the moving direction of the eye even when the upper eyelashes are thick-colored, which may create a strong contrast, like black and long to the extent that they extend over the upper part of the iris or thick to the extent that they partially cover the upper part of the iris and (4) easily identifying a blood vessel to be used for detecting eye motions.

To address these aforementioned problems, the object of the present invention is to provide a method, which (1) has resistance to the fluctuated background light, (2) has also resistance to a moving amount of a camera, (3) is capable of long-time wearing of a camera without firmly fixing it to the head, and (4) easily detecting a blood vessel to be used for detecting eye motions.

Solution to Problem

To solve the aforementioned problem, the eye motion detection method of the present invention, which is executed in an information processing apparatus, comprising the steps of:

(a) entering a reference image of a predetermined area including a area around at least one of eyes, which is captured by an imaging device installed in the vicinity of the front side of at least the one of eyes or at its optically equivalent position, using a one-way mirror and the like;

(b) detecting at least the eye inner corner and the eye outer corner from the reference image;

(c) detecting the white area of the eye from the eye area between the eye inner corner and the eye outer corner on the reference image;

(d) extracting all discriminable blood vessel images from the white area;

(e) determining the blood vessel image to be used for a template blood vessel image among all the blood vessel images;

(f) recording a reference position and reference angle of a horizontal reference of the template blood vessel image in the white area of the eye in the coordinate system;

(g) entering an image for detecting a $n^{th}$ (n is a one or larger integer starting from 1 and gradually increasing in 1 (one) increments) blood vessel image captured by the imaging device;

(h) detecting the $n^{th}$ blood vessel image, which matches the template blood vessel image (hereinafter, simply referred to as the $n^{th}$ matched blood vessel image), from the image for detecting the $n^{th}$ blood vessel image;

(i) recording the position and angle of the detected nth blood vessel in the white area of the eye in the coordinate system;

(j) calculating the moving amount of the n blood vessel based on a difference between the reference position and the position of the detected $n^{th}$ blood vessel in the coordinate system and the eye rotation angle of the detected $n^{th}$ blood vessel based on a difference between the reference angle and the angle of the detected $n^{th}$ blood vessel; and (k) repetitively, executing the steps of the above (g) to (j) assuming that the n is n+1, detecting a $(n+1)^{th}$ blood vessel image, which matches the template blood vessel image, from an image for detecting the n $(n+1)^{th}$ blood vessel image and calculating the moving amount of the $(n+1)^{th}$ blood vessel and the rotation angle.

Moreover, the individual steps involved in the aforementioned method are executed in a calculation part by a program stored in the information processing apparatus and the program is transmitted from storage medium storing the program to a storage part for processing in the information processing apparatus and then executed at the calculation part.

It is preferable that at the step (b) of detecting the eye inner corner and the eye outer corners of the eye and step (c) of detecting the white area of the eye of the present eye motion detection method, the values for a feature vector including the brightness values in an image, which are larger than their thresholds, may be binarized to detect a area with binarized brightness values larger than the thresholds.

It is preferable that at the step (e) of determining a template blood vessel image by the eye motion detection method of the present invention and step (h) of detecting the $n^{th}$ matched blood vessel image, at least one erosion and dilation may be applied to the template blood vessel image and the image used for detecting the $n^{th}$ blood vessel image.

It is preferable that at the step (h) of detecting the $n^{th}$ matched blood vessel image by the eye motion detection method of the present invention, the target blood vessel image may be matched with the template blood vessel image in connection with motions in the vertical, horizontal and/or rotational direction.

It is preferable that at the step (c) of detecting the white area of the eye based on the reference image by the eye motion detection method of the present invention, an iris area and the center of the pupil, which are not contained in the white area of the eye, may be detected, at the step (f) of recording the reference position and reference angle of the template blood vessel image in the coordinate system, a distance from the iris area to the template blood vessel image in the coordinate system and an angle from the horizontal reference line passing through the center of the pupil may be also recorded, and at the step (e) of determining the template blood vessel image and step (h) of detecting the $n^{th}$ matched blood vessel image, the blood vessel image, which is observed in the vicinity of the iris area on the ear side in the white area of the eye and in the vicinity of the horizontal reference line or in the vicinity of the underside of the horizontal reference line, may be selected for determination or detection.

It is preferable that at the step (e) of determining the template blood vessel image by the eye motion detection method of the present invention and step (h) of detecting the $n^{th}$ blood vessel image, as the blood vessel image, which is determined or detected by labeling the individual pixels of the white area of the eye and individual blood vessel images;

(1) by calculating the number of long-side concatenated pixels in a pixel area, which are concatenated under a same label in each blood vessel, a blood vessel image with the maximum number of concatenated pixels is selected, or (2) by calculating a peripheral of the pixel area in which the pixels are concatenated under the same label, a blood vessel image with the maximum length of the peripheral is selected, or (3) By finding the first principal component, which indicates a displacement range relative to the first component axis in the pixel area, in which the pixels are concatenated under the same label and the second principal component, which indicates a displacement range relative to the second component axis in the pixel area, in which the pixels are concatenated in each blood vessel image having the first component axis and the second component axis, which are intersected each other, a blood vessel image, of which the sum of the displacement range values of the first and second principal components is maximum, may be selected.

To solve the aforementioned problem, an eye motion detection device of the present invention is composed of (A) an imaging device installed in the vicinity of at least one eye on the front side, or at its optically equivalent position; and (B) an information processing apparatus, which at least executes the steps of; entering the reference image of the predetermined area including the peripheral of the eye entered from the imaging device (a), detecting at least the eye inner corner and the eye outer corner from the reference image (b), detecting the white area of the eye from the area between the eye inner corner and the eye outer corner on the reference image (c), extracting all the blood vessel images discriminable from the white area of the eye (d), determining a blood vessel image to be used for a template blood vessel image among all the blood vessel images (e), recording the reference position and reference angle of a horizontal reference of the template blood vessel image in the white area of the eye in the coordinate system (f), entering an image for detecting the $n^{th}$ (n is a one or larger integer starting from 1 and gradually increasing in 1 (one) increments) blood vessel image captured by the imaging device (g), detecting the nth matched vessel image (h), recording the detection point and the detection angle of the $n^{th}$ matched blood vessel image in the white area of the eye in the coordinate system (i), calculating a $n^{th}$ moving amount of the eye based on the reference point and the $n^{th}$ detection position in the coordinate system and calculating an eye rotation angle of the $n^{th}$ blood vessel based on a difference between the reference angle and the $n^{th}$ detection angle (j), and executing the aforementioned steps (g) to (j) with setting the n=n+1 to detect the $(n+1)^{th}$ matched blood vessel image from the image for detecting the $(n+1)^{th}$ blood vessel image entered and repeating the calculation of a $n^{th}$ moving amount and a $n^{th}$ rotation angle of the $n^{th}$ blood vessel (k).

Advantageous Effects of the Invention

According to the aforementioned eye motion detection method of the present invention, to address these aforementioned problems, a means, which (1) has resistance to the fluctuated background light, (2) has also resistance to a displacement of a camera, (3) is capable of long-time wearing of a camera without firmly fixing it to the head, and (4) easily detecting a blood vessel to be used for detecting eye motions, is provided, allowing eye positions, angles and motions to be detected at a high accuracy.

It should be noted that the position of the iris may be also detected based on the position, angle and motion of the eye and the direction (the visual line) of the object, which a subject watches, may be detected relative to the pupil at the center of the iris at a higher accuracy.

Taking an example, in case that the visual line stays in the certain direction for longer than a predetermined time period, it is highly probable that a subject watches a known object, in which he/she is very interested or his/her preferable object, though he/she may make an effort to identify or understand what the object is in the case that it is unknown.

BRIEF DESCRIPTION OF DRAWINGS

The FIG. 3a is a flowchart illustrating one example of methods of detecting the eye inner corner and the eye outer corner

FIG. 5a is a view showing one example of eye images, on which halation has occurred due to an auxiliary light or a too strong background light, FIG. 5b is a view showing one example of eye images captured in the place with the dark background light, and FIG. 5c is a view showing one example of eye images with the grayscale contrast enough to recognize a blood vessel of the white area of the eye even under a low-intensity light.

DESCRIPTION OF EMBODIMENTS

Embodiment 1

First of all, the eye motion detection device, method and program of the present invention are explained below.

[Hardware Configuration]

Figure 1:
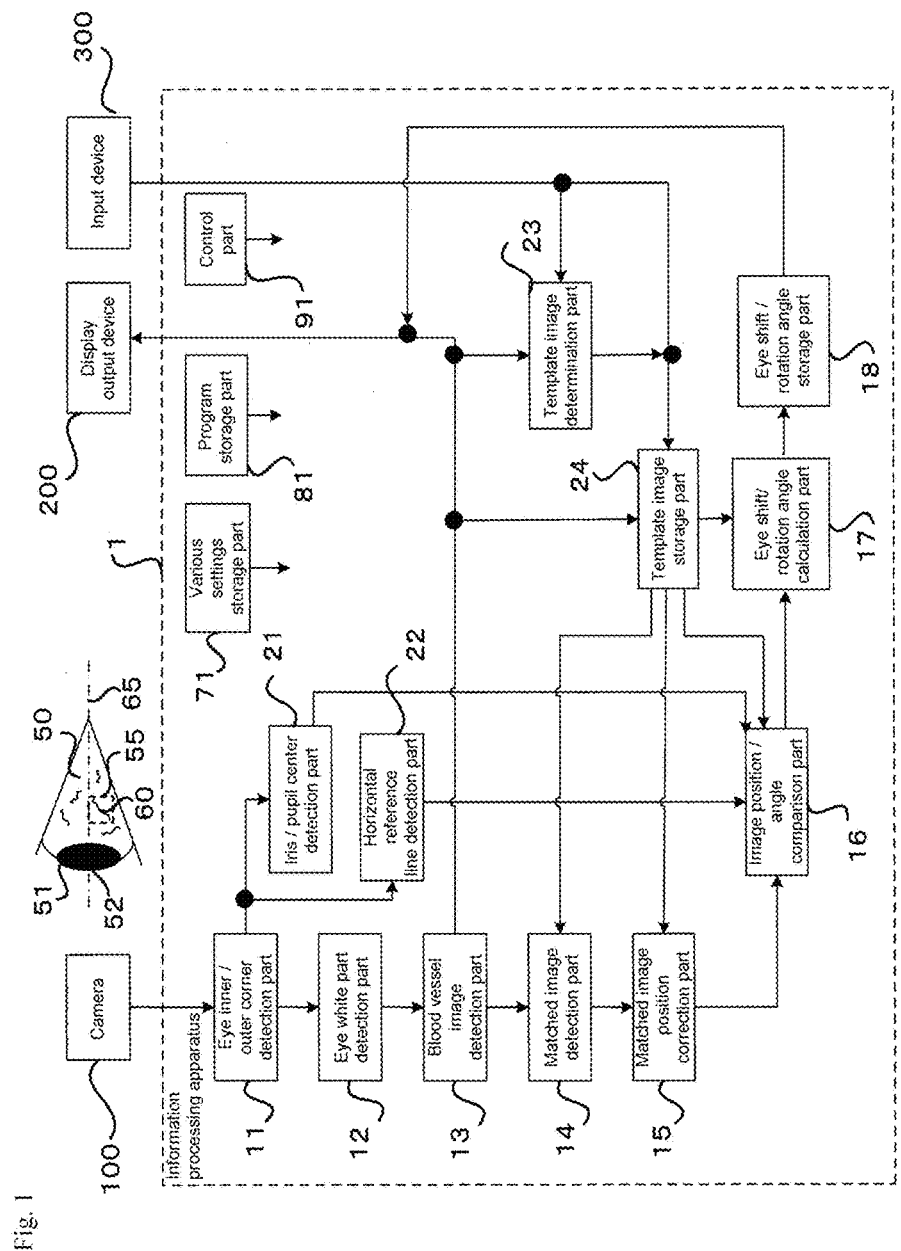
FIG. 1 is a block diagram showing a schematic configuration of an eye motion detection device according to a first embodiment of the present invention.

FIG. 1 is a block diagram showing an eye motion detection device according to an embodiment 1.

An information processing apparatus 1 of an eye motion detection device has incorporated, for instance, a CPU (Central Processing Unit), which is a calculation unit for reading in a program and executing the program steps; a working RAM capable of performing a read/write operation at a high speed; a plurality of memory devices, including non-volatile memory elements, for storing various kinds of programs and the like; an imaging device 100, for instance a camera; a display output device 200, for instance a display; and various kinds of interfaces, which enable electric signals and electric power to be received from and supplied to an input device 300 and the like, for instance a keyboard. The imaging device 100, the display output device 200 and the input device 300 may be connected to the outside of the information processing apparatus or may be incorporated in the information processing apparatus. These various types of components are connected to each other via a bus or serial line, etc.

The CPU is composed of an arithmetic processing unit having, for instance, a program counter, an instruction decoder, various types of calculators, LSU (Load Store Unit), a general-purpose register and others. Programs and data are read in by a drive device from, for instance, an auxiliary memory installed in the information processing apparatus 1 or a memory medium connected to the outside of the information processing apparatus. The memory medium may be a flexible memory medium, for instance, a CD (Compact Disk), DVD (Digital Versatile) or USB (Universal Serial Bus), etc. Moreover, the auxiliary memory may be composed of, for instance, a HDD (Hard Disk Drive) or flash memory.

The programs may be installed in the auxiliary memory, but not limited to the method according to the embodiment 1, by the drive device from an external memory, in which the programs are stored, or may be downloaded from a server or another computer installed at a distant place via interfaces and networks to install in the auxiliary memory. The network may be composed of the Internet, a LAN (Local Area Network), a wireless network and the like. Alternatively, for instance, the programs may have been previously stored (implemented) in the auxiliary memory, ROM (Read Only Memory) (not indicated in the figure) or the like prior to the shipping of the eye motion detection device.

By executing the various kinds of programs installed in the above manner or the various kinds of programs already stored in the device, various types of functions (steps) described later are achieved in the eye motion detection device according to the embodiment 1.

A memory device is composed of memory, for instance, RAM (Random Access Memory), EPPROM (Electrically Erasable and Programmable Read Only Memory) or the like. The interfaces are connected to various kinds of networks and the like to execute the input/output operations of predetermined data and programs from and to the external devices via the network.

The input device 300 is composed of, for instance, various types of input devices including, for instance, a keyboard, a mouse, buttons, a touch pad, and a touch panel, and a mike. The display output device 200 is composed of a display device, for instance, a LCD (Liquid Crystal Display) or a CRT (Cathode Ray Tube). The eye motion detection device may have incorporated various types of output devices, for instance, a printer, a speaker and the like in addition to the display output device 200.

The image input interface of the information processing apparatus is connected to a camera 100. The image input interface outputs image data entered from the camera 100 once to the memory device or auxiliary memory device.

The camera 100 is an imaging device, for instance, a CCD (Charge Coupled Device) camera, a CMOS (Complementary Metal Oxide Semiconductor) camera or the like and outputs data of the captured images via the image input interface. It should be noted that images may be still images or videos.

According to the embodiment 1, the camera 100 captures the eye images of a subject. When the eye image is captured, for instance, a light emitted from a blue LED may be irradiated onto the eye. A light emitted from the blue LED, which increases the contrast of the conjunctival blood vessels (hereinafter, simply referred to as blood vessels) in the eye, must be irradiated onto the white area (containing the sclerotic coat and conjunctiva) of the eye. Narrowing the irradiation range of the blue LED within the white area of the eye may reduce the subject's burden imposed when the eye image is captured. Moreover, to highlight the pupil and capture the grayscale pattern of the iris at a high accuracy, an infrared light emitted from an infrared LED (Light Emitting Diode) may be irradiated onto the eye together with the blue light emitted from the blue LED.

The conventional eye motion measurement device includes a device using a technique called pupillography, by which the infrared light is irradiated onto the eye and the reflected light is measured by an infrared camera to calculate the center of the pupil. As exemplified in FIG. 5b, a relatively intense light is required as an auxiliary light in the dark background. However, both of the techniques have a problem that easily induces halation 66 as shown in FIG. 5a. In case that an intense light is used as an auxiliary light for measurement, in particular, a subject wearing the eye motion detection device may feel discomfort or in some cases, the intense light may be harmful to the eye of the subjects. In contrast, the inventors of the present invention have verified in their experiments that even if the light emitted from the blue LED, which is irradiated onto the white area 50 of the eye shown in FIG. 5c, of the present invention is a very low-intensity light compared with that of the conventional eye motion measurement device, the camera 100 may capture the grayscale contrast enough to recognize the blood vessel image (vessel 60) of the white area of the eye as shown in FIG. 5c. Furthermore, a human being is difficult to sense the glare of a blue light compared with lights of middle-wavelength and long-wavelength due to his/her characteristics of color vision. Accordingly, the eye motion detection device of the present invention may extremely reduce the possibility of occurring halation in the camera 100 and the light used for eye motion measurement causes almost no discomfort in the subject.

[Functional Configuration]

The information processing apparatus 1 has incorporated, as function blocks, which are activated when the CPU executes the programs, an eye inner/outer corner detection part 11, an eye white area detection part 12, a blood vessel image detection part 13, a matched image detection part 14, matched image position correction part 15, an image position/angle comparison part 16, an eye moving amount/rotation angle calculation part 17, an eye moving amount/rotation angle storage part 18, an iris/pupil center detection part 21, a horizontal reference line detection part 22, a template image determination part 23, a template image storage part 24, a various settings storage part 71, a program storage part 81, and a control part 91. Moreover, these function blocks, for instance, inputs/outputs various kinds of information (data) to/from a memory device or an auxiliary device and the memory device and the auxiliary device store the various information output from the individual function blocks.

These function blocks may be configured by means of software. In this case, the individual function blocks may be implemented by the clearly separated programs, or may be implemented by the programs called by other programs, for instance, such as a subroutine and a function. Furthermore, part or all of these function blocks may be configured by hardware such as a LSI (Large Scale Integrated circuit), an IC (Integrated Circuit) and a FPGA (Field Programmable Gate Array).

[General Description of the Eye Motion Detection Method]

Next, details of the eye motion detection method according to the embodiment is specifically described while the corresponding steps executed in the individual function blocks are being explained. First of all, the eye motion detection method according to the embodiment 1 shown in FIG. 1 is generally described.

With the eye motion detection method according to the embodiment 1, first a predetermined template blood vessel (single blood vessel) positioned in the white area of the eye on an eye image in the reference state is selected and position information and angle information thereof is obtained using the selected blood vessel as a template blood vessel image, which serves as a reference image. Then, at the step of measuring eye motions, a blood vessel image, which matches the template blood vessel image in a template matching step, which is performed on a measured eye image (image for blood vessel detection), is detected to obtain the position information and angle information thereof.

[Step of Obtaining the Template Blood Vessel Images]

With the eye motion detection method according to the embodiment 1, the step of obtaining the template blood vessel image is executed prior to the measurement of an eye motion to obtain various kinds of reference information necessary for eye motion measurement. It should be noted that the step of obtaining various kinds of information is executed under the condition, in which eye motions are limited compared with those at the step of measuring the eye motions, when the template blood vessel image is obtained.

According to the embodiment 1, when the template blood vessel image and various reference information are obtained, the eye image is captured fundamentally by irradiating a blue light emitted from the aforementioned blue LED onto the area around the eye blood vessels (white area of the eye). When in addition to blood vessel position data, the iris and the center of the pupil are also used, an infrared LED may be used together to irradiate an infrared light onto the pupil area and the iris area.

Next, at the step of obtaining the template blood vessel image and various kinds of reference information, the eye image of a subject obtained in the reference state is analyzed to obtain vector data on the template blood vessel image in the reference state and position information on the blood vessels. Moreover, if necessary, information on the ellipsoidal parameters for the pupil (for instance, the center point, long axis value, short axis value, inclination (rotation angle of the long axis) of the pupil outline) are obtained.

The information on the template blood vessel image and various reference information are obtained in the aforementioned manner and the various reference information are output to the memory device or the auxiliary memory device for storage. It should be noted that the information on the template blood vessel image position is obtained by means of the coordinates in the X-Y orthogonal coordinate system assuming that the horizontal direction and vertical direction of the eye image in the reference state are the X-axis direction and Y-axis direction, respectively.

[Step of Recognizing the Blood Vessel Position]

Figure 4:
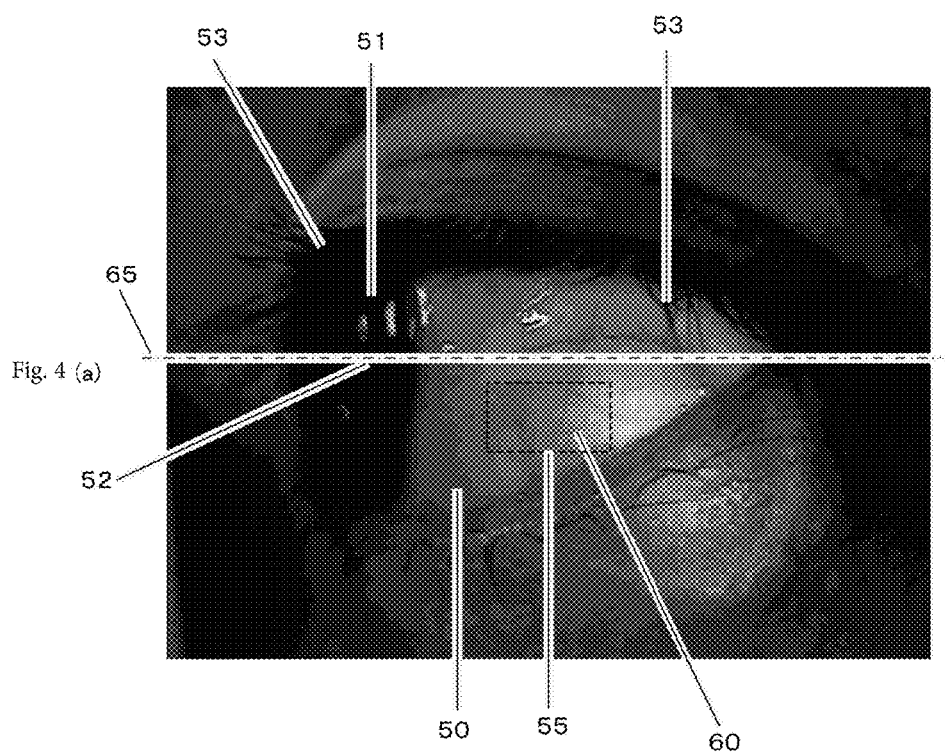
FIG. 4a is a view showing one example of blood vessels in the white area of the eye and FIG. 4b is a view showing one example of selected blood vessel images.
Figure 4:
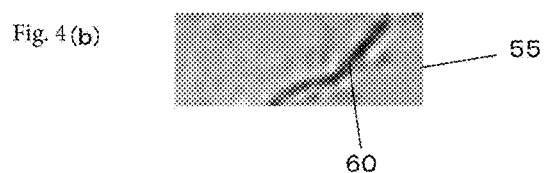

A blood vessel image detection part 13 recognizes the position of a blood vessel 60 and the like in the white area of the eye and outputs the recognized information on the blood vessel 60 position to, for instance the memory device or the auxiliary memory device. The white area of the eye is, as shown in FIGS. 1 and 4, the white area of the eye recognized at the eye white area detection part 12 in the area between the eye inner corner and the eye outer corner recognized at eye inner/outer corner detection part 11 in the eye image. The white area of the eye may be found on the outside of the iris area 51 recognized at iris/pupil center detection part 21 and in the vicinity of the horizontal reference line detected based on the eye inner corner and the eye outer corner, etc. or on the underside of the line. It should be noted that the blood vessel 60 recognized (identified) at the blood vessel image detection part 13, when eye motions are detected at the step of measuring eye motions, the blood vessel (hereinafter, simply referred to as the matched blood vessel), which is matched with the predetermined template blood vessel selected when the template blood vessel image and various reference information are obtained, in the template matching step.

Specifically, at the step of measuring the eye motions, the blood vessel image detection part 13 refers to the reference information stored in the memory device or the auxiliary memory device to obtain the position information on the matched blood vessel (matched blood vessel image) found in the vicinity of the horizontal reference line or in the vicinity of the underside of the line and in the vicinity of the position a predetermined distance away from the iris area 51 at the predetermined point and another predetermined distance away from the center of the pupil 52, in the measured eye image. The blood vessel image detection part 13 outputs the obtained position information (coordinate information) of the matched blood vessel to, for instance, the memory device and the auxiliary memory device. Hereafter, the step executed at the blood vessel image detection part 13 are described in more detail.

First, the blood vessel image detection part 13 reads the position information (coordinate information) on a predetermined template blood vessel image in the reference state, which have been previously obtained at the step of obtaining the template blood vessel image and various reference information, from the memory device or the auxiliary memory device. Second, the blood vessel image detection part 13 sets the search area for identifying the position of the matched blood vessel in the eye image obtained at the step of measuring the eye motions, based on the read position information on the predetermined template blood vessel in the reference state. Specifically, the blood vessel image detection part 13 sets the predetermined shape (for instance, rectangle) focusing on the eye motion angle of the predetermined template blood vessel in the reference state and the rotated points in the eye white area image.

Third, the blood vessel image detection part 13 executes, for instance smoothing on the image in the sear area to filter out noise. Fourth, the blood vessel image detection part 13 executes banalization on the smoothed image in the search area according to pixel values and recognizes a set of the pixels with lower pixel values as a blood vessel. In this step, a plurality of blood vessels are recognized in the search area.

Moreover, the blood vessel image detection part 13 applies the Hilditch's thinning algorithm to the set of blood vessels recognized as a blood vessel to filter out noise. Fifth, the blood vessel image detection part 13 execute depth-first search on the thinned blood vessels to measure the lengths of the blood vessels. Then, the blood vessel image detection part 13 extracts only the blood vessels with the length values larger than the predetermined value among the plurality of recognized blood vessels.

The Hilditch's thinning algorithm assumes that a 3×3 window (pixel area), which refers to the pixels of interest and 8 pixels around them in the search area is a basic processing unit for filtering out noise. Furthermore, the blood vessel image detection part 13 filters out noise using the individual pixels as the pixel of interest while executing raster scanning on the whole image data in the search area for thinning.

Specifically, first, the blood vessel image detection part 13 determines whether or not the pixels of interest in the 3×3 window meet the condition for deletion by thinning previously defined. Second, the blood vessel image detection part 13 deletes the pixel of interest, which meets the deletion condition; namely, it replace the graphic pixels (the pixel in the blood vessel area) with the background pixels (the pixel in the white area of the eye). On the other hand, the blood vessel image detection part 13, if no pixel meets the deletion condition, moves to the next 3×3 window containing the next set of pixels of interest in order of raster scanning to determine whether or not the pixels of interest meet the deletion condition and replaces the graphic pixels with the background pixels.

At the step of filtering out noise by the Hilditch's thinning algorithm, the blood vessel image detection part 13 repeats a series of aforementioned steps on the all the pixels in the search area. Next, the blood vessel image detection part 13 repeats the series of aforementioned steps, until no pixel to be deleted is found in one raster scanning cycle, while executing raster scanning in the search area. Then, the blood vessel image detection part 13 ends the step of filtering out noise by the Hilditch's thinning algorithm when no pixel to be deleted is found in one cycle of raster scanning.

In this case, the position information on the matched blood vessel output from the blood vessel image detection part 13 are the coordinate values in the X-Y orthogonal coordinate system assuming that the horizontal direction and vertical direction of the measured eye image (in the search area) are to be the X-axis direction and Y-axis direction, respectively.

According to the embodiment 1, the predetermined template blood vessel selected in the reference state is found in the manner described below. First, a predetermined search area is defined in the white area of the eye. Second, the series of aforementioned steps, from binarization executed in the blood vessel mage detection part 13 to filtering out noise by the Hilditch's thinning algorithm, are executed on image data in the defined predetermined search area to extract the end points of the plurality of blood vessel in the search area. Then, the predetermined template blood vessel in the reference state is selected among the plurality of extracted blood vessels at a template image determination part 23. These steps may be executed at the blood vessel image detection part 13, from which the result of selection is obtained.

Moreover, at the step of obtaining the template blood vessel and the various reference information, the position an size of the search area used for selecting the predetermined template blood vessel may be defined at the discretion of the user. Furthermore, the criterion for selecting the predetermined template blood vessel among the plurality of extracted blood vessels in the search area may be also defined at the discretion of the user.

However, according to the embodiment 1, it is preferable that the blood vessel found in the vicinity of the horizontal reference line or in the vicinity of the underside of the line and in the vicinity of the position a predetermined distance away from the iris area 51 at the predetermined point and another predetermined distance away from the center of the pupil 52, in the white area of the eye, is selected for the predetermined template blood vessel. It is also preferable that a blood vessel, of which coordinates in the Y-axis direction are the aforementioned another predetermined distance away from the coordinates of the center of the pupil in the Y-axis direction, is selected for the predetermined template blood vessel. By selecting the predetermined template blood vessel in the aforementioned manner, the blood vessel tracking accuracy (matched blood vessel recognition (identification) accuracy) may be improved because of reduced influence of for instance, eyelashes, eyelid motions, visual line movement, etc. (increased possibility that the ends of blood vessels are taken into an eye image), enabling the eye motion angles to be measured more correctly at a higher accuracy. For the same reason, it is preferable that the search area in the reference state is also defined so that it is placed in the vicinity of the horizontal reference line or in the vicinity of the underside of the line and in the vicinity of the position a predetermined distance away from the iris area 51 at the predetermined point and another predetermined distance away from the center of the pupil 52, in the white area of the eye, is selected for the predetermined template blood vessel.

[Step Executed at the Angle Calculation Part]

An eye moving amount/rotation angle calculation part 17 calculates an eye motion angle θ based on the position information on the predetermined template blood vessel selected in the reference state and the position information on the matched blood vessel (a blood vessel corresponding to the predetermined template blood vessel) identified (recognized) at the step of measuring the eye motions.

[Flowchart Illustrating the Step of Detecting Eye Motions]

Figure 2:
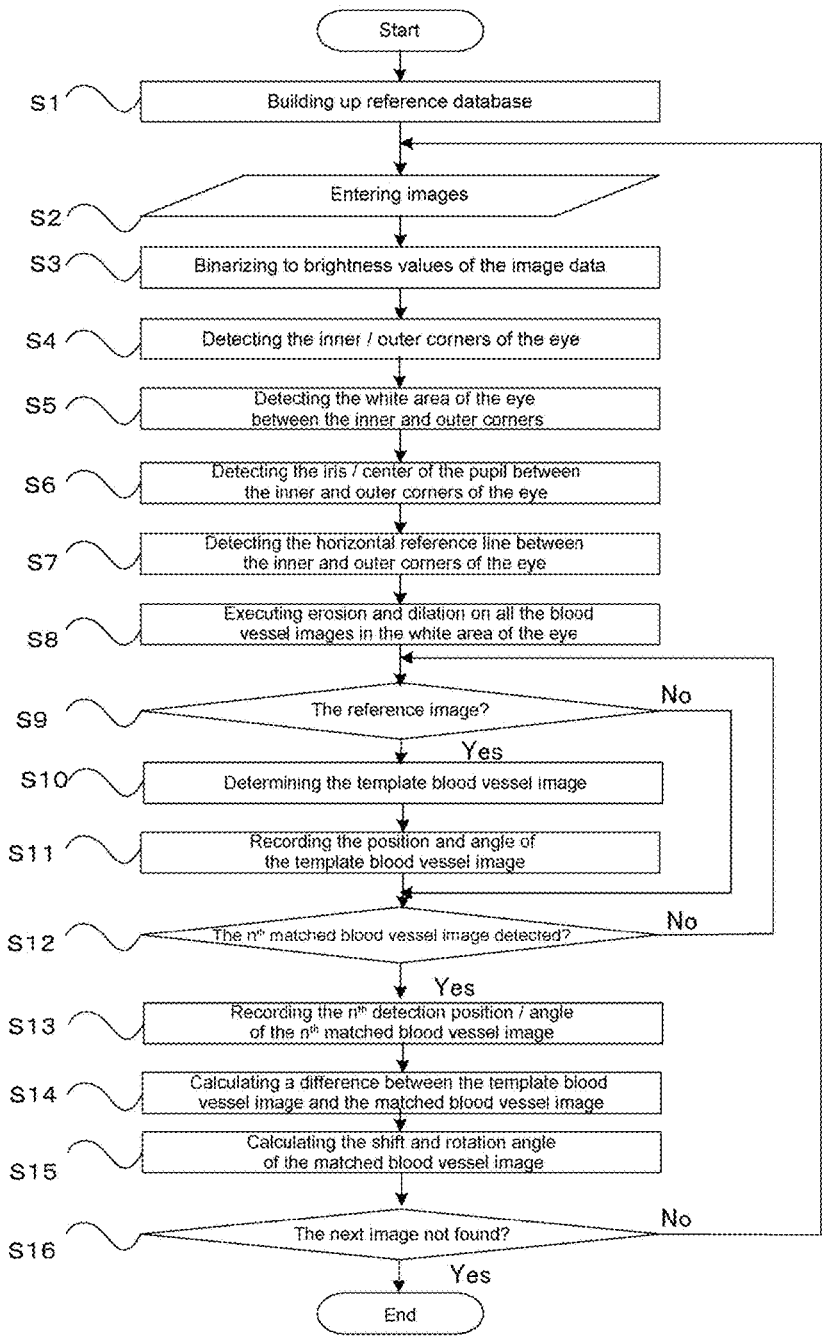
FIG. 2 is a flowchart illustrating a process according to the first embodiment of the present invention.

Next, a specific procedure for detecting the eye motions at the eye motion detection part is explained with reference to FIG. 2. FIG. 2 is a flowchart illustrating the procedure for detecting eye motions executed at the eye motion detection device according to the embodiment 1.

First, prior to actual eye motion detection, a matching database (template image storage part 24) is built up (S1). To build up the matching database, the matching image database is built up based on the feature amount of the predetermined template blood vessel images and the like.

At the step of detecting actual eye motions, newly captured eye images are entered into the information processing apparatus 1 from the imaging device 100 and stored the image data storage part (S2). The brightness values of the image data stored in the image data storage part are binarized (S3). The eye inner corner and the eye outer corner are detected based on the binarized images at the eye inner/outer corner detection part 11 (S4). The white area of the eye found between the eye inner corner/eye outer corner is detected at the eye white area detection part 12 (S5).

Moreover, at the iris/pupil center detection part 21, iris between the eye inner corner/eye outer corner and the center of the pupil are detected based on the image data obtained when an infrared light is irradiated (S6). In addition, at the horizontal reference line detection part 22, the horizontal reference line is detected based on the position information on the detected eye inner corner/eye outer corner (S7).

The erosion and dilation steps are repeated for specified number of times on the all the blood vessel images in the detected white area of the eye (S8) to determine whether or not each of the blood vessel images is the first reference blood vessel image (hereinafter, simply referred to as the reference image) (S9). If it is the first reference image, a predetermined template blood vessel image to be assumed as the reference image is determined based on the defined rules or manually (S10) and various reference information including the template blood vessel image and the position and angle thereof are recorded (S11).

After the template blood vessel image and the various reference information are recorded (S11), or if the blood vessel image is not the first reference image (S9: No), the step of template matching is applied to the next input image to detect the $n^{th}$ (n is a one or larger integer starting from 1 and gradually increasing in 1 (one) increments) matched blood vessel image (S12) and if detected (S12: Yes), the reference information including the position and angle of the image are recorded (S13). If not detected (S12: No), the procedure flow returns to Step 9 to determine whether or not the image is the first reference image and then moves to Step 12 to detect the $n^{th}$ matched blood vessel image.

After the $n^{th}$ matched blood vessel image is detected at S12 and the various reference information on the image are recorded at S13, the position/angle of the template blood vessel image are compared with those of the $n^{th}$ matched blood vessel image to calculate differences between both of the images at an image position/angle comparison part 16 (S14). Next, the moving amount and rotation angle of the eye are calculated based on the differences between the position/rotation angle of the template blood vessel image and those of the $n^{th}$ matched blood vessel image at the eye moving amount/angle calculation part 17 and the calculated position and rotation angle of the eye are stored in the eye moving amount/rotation angle storage part 18 (S15). After then, it is determined whether or not the next image is found (S16), and if it is found (S16: No), the procedure flow returns to S2, in which the next image is entered; if no image found (S16: Yes), the moving amount and rotation angle of the eye calculated at S15 and stored in the eye moving amount/rotation angle storage part 18 are output to a display output device 200 and the procedure terminates.

According to the embodiment 1, the eye motions are measured in the aforementioned manner. It should be noted that according to the embodiment 1, the aforementioned step of detecting eye motions is may be performed by implementing its corresponding eye motion detection program in the eye motion detection device to be executed by the information processing apparatus 1.

The aforementioned eye motion detection technique according to the embodiment 1 allows the eye motions to be calculated based on the position information on the blood vessels in the white area of the eye, which have a higher contrast than the area around the white area of the eye and is not subject to the influence of contraction of the pupil, achieving the eye motion measurement at a higher accuracy.

A step of obtaining the reference information (template) is described below. In the DESCRIPTION section of the present invention, the term "white area of the eye" means the area containing a sclerotic coat and a conjunctiva, and the term "reference state" means, for instance, the state, in which a subject is stress-free and keep in shape, namely the rotation angle of the eye is assumed to be 0 (zero). There are various types (thick, thin, curved, branched, and others) of blood vessels.

(Step of Detecting the White Area (Sclerotic Coat) of Eye)

If color (RGB) data is entered, the data is converted into the YCbCr (or YIQ, HSV) color coordinate system.

$$Y = 0.2989R + 0.5866G + 0.1145B$$

$$Cb = -0.1687R - 0.3312G + 0.5000B$$

$$Cr = 0.5000R - 0.4183G - 0.0816B$$

Where, Y indicates brightness, Cr indicates the color-difference component of red and Cb indicates the color-difference component of blue.

Black and white data is entered, Y is assumed to be the same as the Y component in the YCbCr color coordinate system. In any cases, brightness values are binarized and the areas with values larger than the predetermined threshold are extracted to consider to be the white area of the eye.

(Step of Determining the Template Blood Vessel Image)

To measure horizontal, vertical and rotational eye motions at a single step, SIFT may be used to trace the feature points. On the other hand, the rotational motion component for a human being is not so large, about ±12°, and a soft conjunctiva attached to a sclerotic coat does not allow the conjunctival blood vessels to rotate at the same level as that of the eye; accordingly, measurement may be performed in the horizontal (not including rotational) template matching at a reasonable accuracy.

To measure the horizontal/vertical eye motions simply, the step described below may be followed: erosion is executed on the detected white area of the eye once or twice to remove thin blood vessels, projections and salt-and-pepper noise and then, dilation is executed on the white area of the eye once or twice to leave only thick blood vessels and branch points behind.

A blood vessel image, which is found at the point as close to the black area (cornea) of the eye as possible, on the side of the ear of the black area and in the white area (sclerotic coat) of the eye at the center of the pupil or on the a little underside of the center of the pupil, is selected for the template blood vessel image to avoid blocking the blood vessel image of interest by eyelashes or the eye lid even when the visual line moves in the horizontal direction from the front.

To select the template blood vessel image, the following steps may be followed: for instance, (1) executing labeling on the white area of the eye to select a pixel-concatenated area formed by the largest number of pixels for the template blood vessel image; (2) similarly, executing labeling on the white area of the eye to select the concatenated area of pixels with the longest conference length for the template blood vessel image; or (3) similarly, executing labeling on the white area of the eye and finding the first and second principal components in each of the concatenated areas to select the concatenated area of pixels (namely, the blood vessel image of complicated and characteristic shape), which has the largest sum of errors from both the two principal component axes for the template blood vessel image.

An image blur prevention function as described below has been incorporated to make correct eye motion measurement even if the device attached on the head of a subject is displaced from its original position due to the head or body movement of the subject or due to its own weight.

Peripheral

With the glass-type frame equipped with a camera being correctly attached on the head of the subject, an eye image is captured and defined as the reference image. The eye inner corner and the eye outer corner are extracted in the form of a rectangle on the first eye image, which is the reference image, to find the feature points of the eye inner corner and the eye outer corner and the third feature point is determined according to the criterion described later. Then, on the second and succeeding eye images, the positions of the eye inner corner and the eye outer corner and third feature point are found based on the template blood vessel image created from the first blood vessel image to calculate an Affine matrix. Based on two sets of three point positions of the reference image and the second and succeeding eye images, the second and succeeding eye images may be returned back to the positions of the reference images by Affine conversion.

In this case, the third point has been defined so that the distance between the eye inner corner and the eye outer corner may be used for erosion and dilation, namely a triangle defined by three points may draw a similar figure in both the reference image and the converted images (the second and succeeding images). Moreover, this triangle, which is an isosceles triangle, is defined so that it may be determined on the side where the third point is close to the eye inner corner.

The steps of extracting feature points and of template matching limit the target areas to be processed, in which it is estimated that the eye inner corner and the eye outer corner are found, to reduce erroneous detection and improve the processing speed. At the step of extracting the feature points, a Harris edge detector is used. Moreover, in case that the degree of coincidence is low at the step of template matching, an error may Occur.

(Step Executed at the Angle Calculation Part)

The eye moving amount/rotation angle calculation part 17 calculates the eye motion angle based on the position information on the predetermined template blood vessel selected in the reference state and the position information on the matched blood vessel (blood vessel corresponding to the predetermined template blood vessel) identified (recognized) at the step of measuring eye motions. It should be noted that various kinds of parameters for these reference state have been previously obtained at the step of obtaining the template blood vessel image and various kinds of reference information and stored in, for instance, the memory device or the auxiliary memory device.

As described above, according to the method of the embodiment 1, provided is the method with the advantages of (1) having resistance to a fluctuation in background light; (2) also having resistance to a displacement in camera position with no need for firmly fixing the camera to the head of the subject, which enables long-time wearing; (3) easily detecting eye motions in the moving direction of the eye even when the upper eyelashes are long and thick-colored; and (4) easily identifying a blood vessel to be used for detecting eye motions.

Embodiment 2

The step of executing horizontal/vertical template matching, which is the second method, is described below. At this step, brightness value data is used as a feature vector. With the center t[k,l] of the template image placed at a point (i,j) in the input image f[i,j], the similarity between the overlapped local areas is calculated while raster scanning is being executed on the point (i,j) to determine the position with the largest similarity. The methods to determine the similarity include those using "residual sum of squares" capable of high-speed processing; using "cross relation"; using "coefficient of correlation" having resistance to a fluctuation in brightness; and normalizing based on the image size or the brightness value. The step of normalizing may be executed as a pre-process of template matching to address any inconsistency in size. Moreover, if any fluctuation occurs in brightness of illuminating light irradiated on the eye, Zero-mean Normalized Cross Correlation (ZNCC), in which mean brightness values of the individual images are subtracted from the pixel value, is effective and expected to measure at a high accuracy, though it has the disadvantages of a large amount of calculation and slow processing speed.

When a color camera is used, the CamShift method may be used as the third method, which focusing on each of RGB histograms of the input image without converting into brightness values, the template is moving amounted to the position closer to the features of the histograms in the image contained in the current frame (object tracking).

[General Description of Video Stabilization Control]

Figure 3:
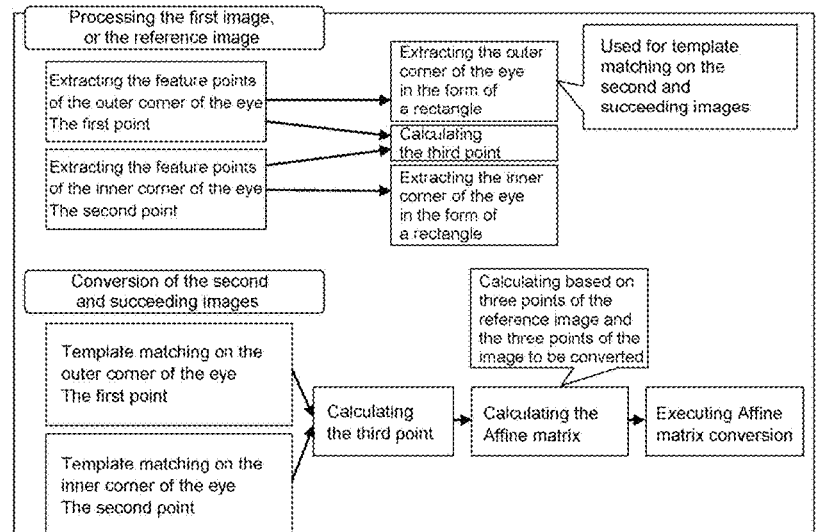
FIG. 3b is a view showing one example of steps of extracting the eye inner corner and the eye outer corner in the rectangular form.
Figure 3:
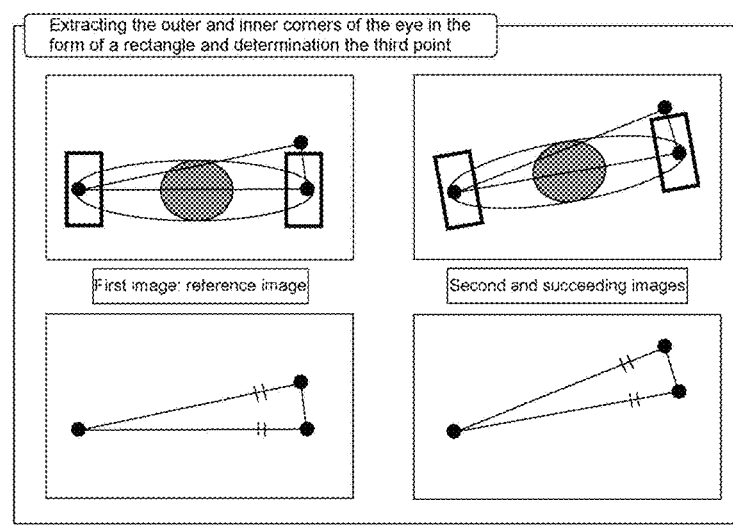

An image blur prevention function (video stabilization control) shown in FIG. 3 may be incorporated to make correct eye motion measurement even if the device attached on the head of a subject is displaced due to the head or body movement of the subject or due to its own weight.

With the glass-type frame equipped with a camera being correctly attached on the head of the subject, an eye image is captured and defined as the reference image. The eye inner corner and eye outer corner are extracted in the form of a rectangle on the first eye image, which is the reference image, to find the feature points of the eye inner corner and eye outer corner and the third feature point is determined according to the criterion described later. Then, on the second and succeeding eye images, the positions of the eye inner corner and eye outer corner and the third feature point are found based on the template image created from the first eye image to calculate an Affine matrix. Based on two sets of three point positions of the reference image and the second and succeeding eye images, the second and succeeding eye images may be returned back to the positions of the reference image by Affine conversion.

In this case, the third point has been defined that the distance between the eye inner corner and eye outer corner may be used for erosion and dilation, namely triangles defined by three points may draw a similar figure in both the reference image and the converted images (the second and succeeding images). Moreover, this triangle, which is an isosceles triangle, is defined so that it may be determined on the side where the third point is close to the eye inner corner.

The steps of extracting feature points and of template matching limit the target areas to be processed, in which it is estimated that the eye inner corner and the eye outer corner are found, to reduce erroneous detection and improve the processing speed. At the step of extracting the feature points, a Harris edge detector is used. Moreover, in case that the degree of coincidence is low at the step of template matching, an error may occur.

FIG. 4 is a view showing one example of the blood vessels in the white area of the eye and one example of selected template blood vessel images. According to the method of an embodiment 1, even if the glass-type frame is displaced from the subject face, eye motions may be measured with no trouble as far as the degree of tilt is at the same level as that when it is used daily.

REFERENCE SIGNS LIST

1 Information processing apparatus
11 Eye inner/outer corner detection part
12 Eye white area detection part
13 Blood vessel image detection part
14 Matched image detection part
15 Matched image position correction part
16 Image position/angle comparison part
17 Eye moving amount/rotation angle calculation part
18 Eye moving amount/rotation angle storage part
21 Iris/pupil center detection part
22 Horizontal reference line detection part
23 Template image determination part
24 Template image storage part
50 Eye white area
51 Iris area
52 Center of pupil
53 Eyelashes
55 Detection area (matching area)
60 Blood vessel
65 Horizontal reference line
66 Halation
71 Various settings storage part
81 Program storage part
91 Control part
100 Imaging device (Camera)
200 Display output device
300 Input device

The invention claimed is:

1. An eye motion detection method, which is incorporated in an information processing apparatus, comprising the steps of:
   (a) entering a reference image of a predetermined area including an area around at least one of eyes, which is captured by an imaging device installed in the vicinity of the front side of at least the one of eyes or at its optically equivalent position;
   (b) detecting at least an eye inner corner and an eye outer corner of the eye from the reference image;
   (c) detecting the white area of the eye from the eye area between the eye inner corner and the eye outer coroner of the reference image;
   (d) extracting all discriminable blood vessel images from the white area;
   (e) determining a blood vessel image to be used for a template blood vessel image among the all blood vessel images;
   (f) recording a reference position and the reference angle of a horizontal reference of the template blood vessel image in the white area of the eye in the coordinate system;
   (g) entering an image for detecting a $n^{th}$ (n is a one or larger integer starting from 1 and gradually increasing in 1 (one) increments) blood vessel detecting image captured by the imaging device;
   (h) detecting the $n^{th}$ blood vessel image, which matches the template blood vessel image (hereinafter, simply referred to as the $n^{th}$ matched blood vessel image), from the $n^{th}$ blood vessel detecting image;
   (i) recording the $n^{th}$ detected position and the $n^{th}$ detected angle of the detected $n^{th}$ matched blood vessel image in the white area of the eye in the coordinate system;
   (j) calculating a $n^{th}$ moving amount of the eye based on a difference between the reference position and the $n^{th}$ detected position in the coordinate system and calculate a $n^{th}$ eye rotation angle based on a difference between the reference angle and the $n^{th}$ detected angle; and
   (k) repetitively, executing the above step (g) to step (j) with setting the n=n+1, detecting a $(n+1)^{th}$ matched blood vessel image from an entered $(n+1)^{th}$ blood vessel detecting image and calculating a $(n+1)^{th}$ moving amount and a $(n+1)^{th}$ rotation angle of the $(n+1)^{th}$ matched blood vessel image.

2. The eye motion detection method defined in claim 1, wherein step (b) of detecting the eye inner corner and eye outer corner and step (c) of detecting the white area of the eye feature vector values including the brightness values of the binarized image and detecting areas whose binarized brightness value is higher than or equal to its threshold value.

3. The eye motion detection method defined in claim 1, wherein in step (e) of determining the template blood vessel image and step in (h) of detecting the $n^{th}$ matched blood vessel image, erosion and dilation are executed at least once, respectively, on the template blood vessel image and the individual $n^{th}$ blood vessel detection images.

4. The eye motion detection method defined in claim 1, wherein in step (h) of detecting the $n^{th}$ matched blood vessel image, the $n^{th}$ matched blood vessel image is matched with the template blood vessel image in accordance with a moving amount in the vertical, horizontal and/or rotational direction.

5. The eye motion detection method defined in claim 1, wherein in step (c) of detecting the white area from the reference image, an iris area which are not included in the white area of the eye and the center of a pupil are detected,
   wherein in step (f) of recording a reference position and a reference angle of the template blood vessel image in the coordinate system, a distance from the iris area to the template blood vessel image in the coordinate system and the angle from the horizontal reference line passing through the center of the pupil,
   wherein in step (e) of determining the template blood vessel image and in step (h) of detecting the $n^{th}$ matched blood vessel image, termination or detection with selection of a blood vessel image, which is found in the vicinity area of the iris area on an ear side in the white area of the eye and in the vicinity area in the lower side area of the horizontal reference line.

6. The eye motion detection method defined in claim 1, wherein in step (e) of determining the template blood vessel image and in step (h) of detecting the $n^{th}$ matched blood vessel image, labeling the individual pixels of the white area of the eye and individual blood vessel images, wherein the blood vessel image is determined or detected;
   (1) by calculating the concatenated number of long-side concatenated pixel area with same label in each blood vessel image and select a blood vessel image which has the largest concatenated number, or
   (2) by calculating a peripheral length of the concatenated pixel area with same label in each blood vessel image and select a blood vessel image which has the largest peripheral length, or
   (3) by obtaining the first principal component which indicates a displacement range relative to the first component axis in the concatenated pixel area with same label, and the second principal component which indicates a displacement range relative to the second component axis in the concatenated pixel area with same label, and selecting a blood vessel image which has the largest sum value of the displacement range of the first component axis and the displacement range of the second component axis.

7. The eye motion detection method defined in claim 1, wherein obtaining at least the eye inner corner and the eye outer corner as the two feature points from the reference image, and determining the third feature in accordance with a predetermined triangle, and suppressing blur in the $n^{th}$ blood vessel detecting image by setting the triangle formed by the three feature points are similar form.

8. A program executing the steps in the eye motion detection method of claim 1.

9. A non-transitory storage medium storing the program in claim 8.

10. An eye motion detection device comprising:
(A) an imaging device installed in the vicinity of at least one of eyes on the front side, or at its optically equivalent position; and
(B) an information processing apparatus, which at least executes the steps of; entering the reference image of the predetermined area including the peripheral of the eye entered from the imaging device (a); detecting at least the eye inner corner and the eye outer corner from the reference image (b); detecting the white area of the eye from the area between the eye inner corner and the eye outer corner on the reference image (c); extracting all the blood vessel images discriminable from the white area of the eye (d); determining a blood vessel image to be used for a template blood vessel image among all the blood vessel (e); recording a reference position and a reference angle of a horizontal reference in the coordinate system of the template blood vessel image in the white area of the eye (f); entering an image for detecting a $n^{th}$ (n is a one or larger integer starting from 1 and gradually increasing in 1 (one) increments) blood vessel image captured by the imaging device (g); detecting a $n^{th}$ blood vessel image, which matches the template blood vessel image (h); recording the detection point and detection angle of the $n^{th}$ blood vessel image, which matches the template blood vessel image, in the white area of the eye in the coordinate system (i); calculating a moving amount of the $n^{th}$ blood vessel based on the reference point and detection position of the $n^{th}$ blood vessel in the coordinate system and calculating an eye rotation angle of the $n^{th}$ blood vessel based on a difference between the reference angle and detection angle of the $n^{th}$ blood vessel (j); and executing the aforementioned steps (g) to (j) with setting the n=n+1 to detect the $(n+1)^{th}$ blood vessel image, which matched the template blood vessel image from the image for detecting the $(n+1)^{th}$ blood vessel image entered; and step (k) of repeating the calculation of the moving amount and rotation angle of the $n^{th}$ blood vessel.

11. The eye motion detection method defined in claim 2, wherein in step (e) of determining the template blood vessel image and in step (h) of detecting the $n^{th}$ matched blood vessel image, erosion and dilation are executed at least once, respectively, on the template blood vessel image and the individual $n^{th}$ blood vessel detection images.

12. The eye motion detection method defined in claim 2, wherein in step (h) of detecting the $n^{th}$ matched blood vessel image, the $n^{th}$ matched blood vessel image is matched with the template blood vessel image in accordance with a moving amount in the vertical, horizontal and/or rotational direction.

13. The eye motion detection method defined in claim 3, wherein in step (h) of detecting the $n^{th}$ matched blood vessel image, the $n^{th}$ matched blood vessel image is matched with the template blood vessel image in accordance with a moving amount in the vertical, horizontal and/or rotational direction.

14. The eye motion detection method defined in claim 11, wherein in step (h) of detecting the $n^{th}$ matched blood vessel image, the $n^{th}$ matched blood vessel image is matched with the template blood vessel image in accordance with a moving amount in the vertical, horizontal and/or rotational direction.

15. The eye motion detection method defined in claim 2, wherein in step (c) of detecting the white area from the reference image, an iris area which are not included in the white area of the eye and the center of a pupil are detected,
wherein in step (f) of recording a reference position and a reference angle of the template blood vessel image in the coordinate system, a distance from the iris area to the template blood vessel image in the coordinate system and the angle from the horizontal reference line passing through the center of the pupil,
wherein in step (e) of determining the template blood vessel image and in step (h) of detecting the $n^{th}$ matched blood vessel image, termination or detection with selection of a blood vessel image, which is found in the vicinity area of the iris area on an ear side in the white area of the eye and in the vicinity area in the lower side area of the horizontal reference line.

16. The eye motion detection method defined in claim 3, wherein in step (c) of detecting the white area from the reference image, an iris area which are not included in the white area of the eye and the center of a pupil are detected,
wherein in step (f) of recording a reference position and a reference angle of the template blood vessel image in the coordinate system, a distance from the iris area to the template blood vessel image in the coordinate system and the angle from the horizontal reference line passing through the center of the pupil,
wherein in step (e) of determining the template blood vessel image and in step (h) of detecting the $n^{th}$ matched blood vessel image, termination or detection with selection of a blood vessel image, which is found in the vicinity area of the iris area on an ear side in the white area of the eye and in the vicinity area in the lower side area of the horizontal reference line.

17. The eye motion detection method defined in claim 4, wherein in step (c) of detecting the white area from the reference image, an iris area which are not included in the white area of the eye and the center of a pupil are detected,
wherein in step (f) of recording a reference position and a reference angle of the template blood vessel image in the coordinate system, a distance from the iris area to the template blood vessel image in the coordinate system and the angle from the horizontal reference line passing through the center of the pupil,
wherein in step (e) of determining the template blood vessel image and in step (h) of detecting the $n^{th}$ matched blood vessel image, termination or detection with selection of a blood vessel image, which is found in the vicinity area of the iris area on an ear side in the white area of the eye and in the vicinity area in the lower side area of the horizontal reference line.

18. The eye motion detection method defined in claim 11, wherein in step (c) of detecting the white area from the reference image, an iris area which are not included in the white area of the eye and the center of a pupil are detected,
wherein in step (f) of recording a reference position and a reference angle of the template blood vessel image in the coordinate system, a distance from the iris area to the template blood vessel image in the coordinate system and the angle from the horizontal reference line passing through the center of the pupil, wherein in step (e) of determining the template blood vessel image and in step (h) of detecting the $n^{th}$ matched blood vessel image, termination or detection with selection of a blood vessel image, which is found in the vicinity area of the iris area on an ear side in the white area of the eye and in the vicinity area in the lower side area of the horizontal reference line.

19. The eye motion detection method defined in claim 12, wherein in step (c) of detecting the white area from the reference image, an iris area which are not included in the white area of the eye and the center of a pupil are detected, wherein in step (f) of recording a reference position and a reference angle of the template blood vessel image in the coordinate system, a distance from the iris area to the template blood vessel image in the coordinate system and the angle from the horizontal reference line passing through the center of the pupil, wherein in step (e) of determining the template blood vessel image and in step (h) of detecting the $n^{th}$ matched blood vessel image, termination or detection with selection of a blood vessel image, which is found in the vicinity area of the iris area on an ear side in the white area of the eye and in the vicinity area in the lower side area of the horizontal reference line.

20. The eye motion detection method defined in claim 13, wherein in step (c) of detecting the white area from the reference image, an iris area which are not included in the white area of the eye and the center of a pupil are detected, wherein in step (f) of recording a reference position and a reference angle of the template blood vessel image in the coordinate system, a distance from the iris area to the template blood vessel image in the coordinate system and the angle from the horizontal reference line passing through the center of the pupil, wherein in step (e) of determining the template blood vessel image and in step (h) of detecting the $n^{th}$ matched blood vessel image, termination or detection with selection of a blood vessel image, which is found in the vicinity area of the iris area on an ear side in the white area of the eye and in the vicinity area in the lower side area of the horizontal reference line.

\* \* \* \* \*

UNITED STATES PATENT AND TRADEMARK OFFICE
CERTIFICATE OF CORRECTION

PATENT NO.        : 10,311,583 B2
APPLICATION NO.   : 15/579241
DATED             : June 4, 2019
INVENTOR(S)       : Kiyoshi Hoshino Page 1 of 1

It is certified that error appears in the above-identified patent and that said Letters Patent is hereby corrected as shown below:

In the Claims

Column 17, Line 43, Claim 1, delete "coroner" and insert -- corner --

Signed and Sealed this
Twenty-seventh Day of August, 2019

Andrei Iancu
*Director of the United States Patent and Trademark Office*